United States Patent [19]
Goldsmith

[11] 3,985,017
[45] Oct. 12, 1976

[54] GASEOUS CONTAMINATE DOSIMETER AND METHOD

[75] Inventor: Robert L. Goldsmith, Belmont, Mass.

[73] Assignee: Abcor, Inc., Cambridge, Mass.

[22] Filed: Jan. 2, 1975

[21] Appl. No.: 537,908

[52] U.S. Cl. ................................ 73/23; 23/232 R; 23/254 R
[51] Int. Cl.² .......................................... G01N 31/00
[58] Field of Search............ 73/421.5, 23; 23/232 R, 23/254 R

[56] References Cited
UNITED STATES PATENTS

| | | | |
|---|---|---|---|
| 2,234,499 | 3/1941 | McAllister | 73/23 |
| 3,481,179 | 12/1969 | Howarth | 73/27 R |
| 3,607,084 | 9/1971 | Mackey | 73/27 R |
| 3,681,027 | 8/1972 | Smith | 23/254 R |
| 3,924,219 | 12/1975 | Braun | 338/34 |

Primary Examiner—James J. Gill
Assistant Examiner—Anthony V. Ciarlante
Attorney, Agent, or Firm—Richard P. Crowley

[57] ABSTRACT

A gaseous contaminate personal dosimeter which comprises a container; an inert porous thin barrier element forming one side of the container, the barrier element adapted to permit the diffusion of the gaseous contaminates that are to be determined into the interior of the container; and a gaseous contaminate-collecting medium within the container and positioned opposite the barrier element to collect gaseous contaminate diffused from the ambient atmosphere through the barrier element; and means to inhibit convection movement of the diffused gases within the container, whereby the dosimeter permits the determination of gaseous contaminate in proportion to ambient concentrations independent of ambient convection patterns.

17 Claims, 3 Drawing Figures

GASEOUS CONTAMINATE DOSIMETER AND METHOD

BACKGROUND OF THE INVENTION

Dosimetry is an extension to the present fixed-site air pollution sampling systems. Previous to about 1950, air pollution measurements were concerned more with property effects than with health effects. There has been an increased requirement to correlate health effects with the quality of the air to which the general population is exposed. Prior to 1950, various investigators in the area of industrial hygiene was engaged in activity directed to workroom atmospheres. A considerable amount of the methods and instruments developed for industrial hygiene investigations have been adapted to the study of air pollution measurements.

In the area of industrial hygiene, it has been recognized that, at an early date, it is desirable to provide workers with portable instrumentation to measure exposure or dosage to dust, certain gases and radiation. There has been some development in miniature sampling instrumentation for installation on some segments of the worker population. For example, a passive personal monitoring device for gaseous contaminates based on molecular diffusion of the gas to be measured, such as sulfur dioxide, has been proposed (see "American Industrial Hygiene Association Journal," Vol. 34, pgs. 78–81, 1973).

Instrumenting workers with personal sampling equipment has met with certain implementation problems. Problems relating to subject performance include: failure to wear the equipment; failure to maintain the equipment; and failure to operate the equipment.

In the development of instrumental dosimeters, certain additional limitations have been encountered, including, but not limited to: size and weight (restriction on subject freedom of movement); cost (inhibits testing by large population segment); need for power supply; high maintenance requirements; drift in instrument response (leads to erroneous measurements); and sensivity to changes in temperature and humidity.

Another approach has been to use indicator tubes, for field measurement. However, these show poor accuracy (<±50%) due to: variability in quality control in tube manufacture; error in test subject judgement; degradation of color developed with time; variation in sample flow rate with time (a flow-through system is required); and variation in ambient temperature (affects reaction rate).

A third method has been to use exposure plates, such as badges, which are completely passive. This approach has been highly successful for radiation badges.

These nonburdensome radiation badges, which are in widespread industrial use, are virtually fool-proof if simply worn. The sensing elements are issued and collected periodically with the collected film being processed efficiently in a central location. An analogous system for air pollution dosimetry would be most valuable; however, the major limitation encountered is that a badge of this nature does not respond to pollutant concentration, but rather to a complicated interaction of concentration and ambient air circulation patterns. Thus, a personal passive dosimeter and method of determining gaseous contaminates, which would overcome the disadvantages of prior art devices, is most desirable.

SUMMARY OF THE INVENTION

My invention relates to a dosimeter for measuring the concentration of gaseous contaminates in an ambient atmosphere, and to a method of utilizing such dosimeter and techniques to measure such gaseous pollutants. In particular, my method relates to a low-cost, passive, personal dosimeter which is light-weight and highly accurate, and provides for analysis to be formed at a central station, so that the results are not dependent on test-subject skill. More particularly, my invention is directed to a personal dosimeter which provides for an accurate measure of gaseous contaminates to which the dosimeter is exposed in proportion to ambient contaminate concentration, and independent of air-convection patterns about the dosimeter.

My gaseous contaminate dosimeter comprises a container having an inert porous sheet barrier element adapted to permit the diffusion of the gas, such as air, with the gaseous contaminates into the interior of the container; a collecting medium within the container adapted to collect the gaseous contaminates quantitatively which are diffused through the barrier element; and a means to provide for mechanical support of the barrier element, to hold the collecting material into place and to inhibit or prevent convection movement of the diffused gases within the interior of the container. My dosimeter is thus designed to provide for the determination of a concentration of gaseous contaminates, such as the oxides of sulfur; e.g., sulfur dioxide, the oxides of nitrogen; e.g., nitrogen dioxide, ozone, carbon monoxide, hydrogen sulfide, vinyl chloride and other organic vapors or gaseous contaminates in the ambient atmosphere, in proportion to ambient concentrations in the atmosphere, and substantially independent of ambient air-convection patterns about the dosimeter.

Gaseous contaminates may be introduced into the interior of my dosimeter only by diffusion through a porous thin barrier sheet which forms one side of the dosimeter. My barrier sheet provides a stagnant air layer of a diffusive barrier directly inside the container, which barrier layer is substantially unaffected by circulatory air patterns which exist exterior to the dosimeter. My dosimeter is so designed that the resistance to mass transfer in the stagnant air layer adjacent the barrier sheet greatly exceeds the resistance associated with mass transfer to the porous sheet exterior of the dosimeter. Thus, in my dosimeter, the contaminate gaseous concentration at the exterior of the porous barrier sheet will always be at or near the ambient concentration, with negligible convective transfer resistance. My dosimeter samples ambient air and the gaseous contaminates therein in proportion to the ambient contaminate concentration, and independent of air-convection patterns in the ambient atmosphere. In particular, my dosimeter includes a means to inhibit or prevent convection movement of the diffused gases within the dosimeter.

DESCRIPTION OF THE EMBODIMENTS

Figure 2:
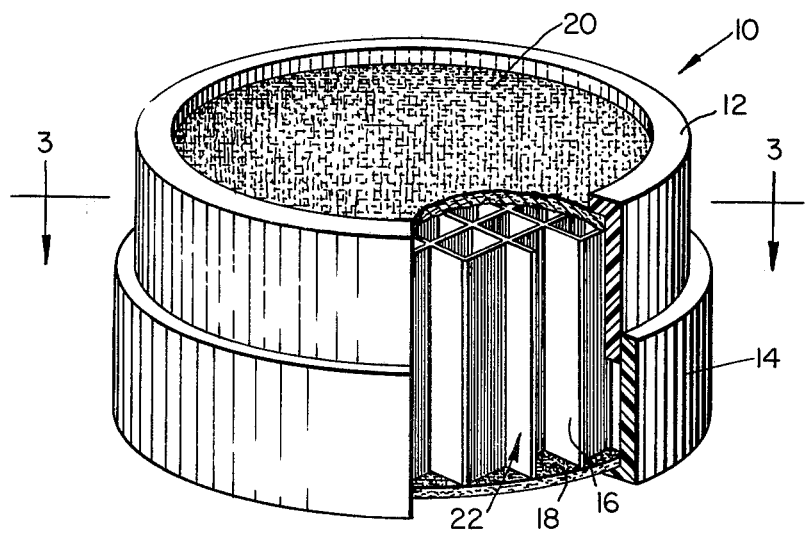
FIG. 2 is an illustrative perspective partially crosssectional view of my personal dosimeter.
Figure 3:
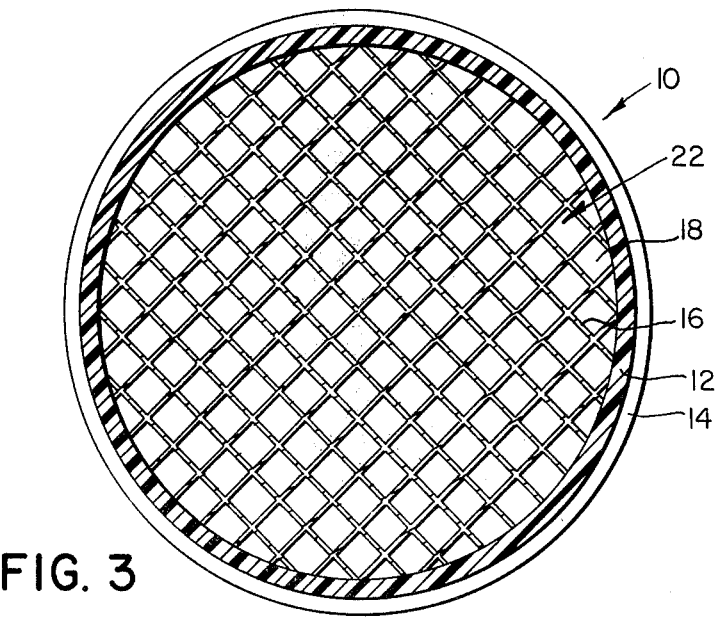
FIG. 3 is a cross-sectional view along lines 3—3 of the dosimeter of FIG. 2.

FIGS. 2 and 3 illustrate a preferred embodiment of my personal passive dosimeter 10 which includes a closed plastic container having housing elements 12 and 14, the element 12 adapted to be fitted in a slidable fluid-tight manner within housing element 14 to form a gas-tight container. Adjacent one wall of the container is a contaminate-collective matrix element 18, while the opposite wall of the container contains a thin inert porous barrier sheet material 20 to be exposed to the ambient air with the gaseous contaminate. In the embodiment illustrated, between the inert porous sheet 20 and the collective matrix sheet 18 is a honeycomb air stagnation baffle-collecting matrix system 16 composed of a plurality of elongated, uniformly spaced, honeycomb passageways 22 which extend from the interior face of the barrier sheet 20 to the collecting face of the collector 18, and which separates the collective matrix 18 from the inert barrier sheet 20. The honeycommb spacer 16 provides for mechanical support of the thin porous barrier sheet material 20, and in addition, retains and holds the contaminate-collective matrix sheet material 18 into place and adjacent the interior adjacent wall of the dosimeter 10. Another purpose of the spacer material on the honeycomb baffles therein is to prevent or inhibit convection of any diffused air which diffuses through the barrier sheet 20 and migrates into the interior of the dosimeter 10.

In the selection of an inert porous sheet barrier element, I prefer to select a thin porous inert material which has a maximum pore size and a minimum thickness, since these factors minimize the surface area available on the barrier sheet for any contaminate adsorption or reaction. It should be noted that the parameters controlling the gas diffusion through the inert barrier sheet 18 are the porosity and thickness, while the pore diameter does not enter into the diffusion equation, provided only that the pores are of a sufficient size to permit the gaseous stream and contaminates to be passed therethrough.

Typical pore sizes of the barrier sheet may range from about 5 to 50 microns, with porosities ranging from 50 to 95%, and with thicknesses ranging from about 0.01 cm to 0.8 cm.

Typical interface barrier elements may include, but not be limited to, porous polymeric materials, such as porous olefins like polyethylene and polypropylene, and inert halocarbons like polytetrafluoroethylene. Such materials may be prepared by sintering particles into sheet form. The materials include fiber-glass woven of nonwoven filter-type sheets, porous glass, such as Vycor and ceramic frits, sintered metals like stainless steel, and other such materials. The desired characteristics of the barrier sheet should be chemical inertness with regards to the diffusion contaminate; that is, the material should not affect adsorption, absorption or chemical reaction with the gaseous contaminate to be measured; high porosity; adequate mechanical strength; uniform properties; and desirable low-cost and easily obtainable materials. Commercially available barrier materials would include a Teflon filter having a thickness of 0.01 to 0.5 cm, a pore size of 5 to 10 microns and a porosity of about 70%. Other barrier materials would include sintered polyethylene and polypropylene sheets, which sheets commercially range in thickness from about 0.15 cm to about 0.6 cm with a pore size ranging from about 50 microns.

The contaminate matrix or element is illustrated as a separate removable element to be inserted within the dosimeter, or where a throw-away dosimeter is to be employed or a one-time use dosimeter is employed, it may be permanently attached to the wall surface of the dosimeter. The contaminate-collector element may comprise a means for the collection or entrapment of the gaseous contaminates to be determined. Typically and in the preferred embodiment, the collector element should be an easily insertable and removable sheet material, coated, treated or otherwise impregnated with one or more substances to react with or to collect the gaseous contaminates in a quantitative manner, and suitable for use such that the contaminates so collected may be rapidly determined to the desired concentration levels.

The collector element should contain an excess of the chemical that absorbs or reacts with the gaseous contaminates, and the contaminates should be retained within or on the collector element; that is, be stable, so that the material may be subsequently analyzed at a central laboratory. For example, in the determination of oxides of sulfur, such as sulfur dioxide, the collector sheet may comprise sintered metal particles which are selectively poisoned by the oxides of sulfur, such as a reactive lead-oxide sheet, the amount of sulfide contaminate then being easily determined, either by chemical analysis or by measurement of the electrical conductivity of the poisoned metal sheet in comparison to a nonpoisoned or standard poisoned metal sheet. Another collecting sheet comprises a filter paper impregnated with a solution of potassium hydroxide and a glycerine solution for the collection of acidic gases like hydrogen sulfide, sulfur dioxide and nitrogen dioxide, etc.

For the collection and determination of vinyl chloride or other organic vapors, the collecting medium may comprise a sheet containing or coated with activated carbon or other adsorbent or absorbent particles. On analysis, the gas collected would be displaced by solvent extraction and analyzed by gas or vapor chromatography.

For the purpose of illustration, my personal dosimeter of FIGS. 2–3 may use a coated surface, wherein the coating will be in substantial excess of a chemical that reacts rapidly and completely; for example, with ozone, to form a stable compound. Typical support mediums for the sheet-collecting means would include paper, tetrafluoroethylene or other polymeric sheets, and metal sheets such as aluminum foil. In selecting the nature of the coated surface of the support sheet, the stability of the reactant itself; that is, its shelf life, should be determined, the stability of the compound to be formed by the gaseous contaminate, and a lower detection limit or the sensitivity of the materials, interference, as well as the range and precision of the chemical analysis to be employed should be considered.

My dosimeter, to be suitable for use, must collect a sample in proportion to the ambient concentration of the contaminant; that is, it must collect an air sample independent of air circulation patterns in the vicinity of the dosimeter or movement of the subject wearing the dosimeter. This can be accomplished by creating a diffusional resistance within the dosimeter which substantially exceeds; e.g., over five times, the diffusional resistance of convective mass transfer exterior to the dosimeter. One such approach has been to utilize a capillary leading to an aqueous sorption medium for SO$_2$ (see citation supra).

In my dosimeter (FIGS. 2–3), the dead air space corresponds to the volume within the "honeycomb" spacer between the porous sheet and surface collector. The high porosity of the porous sheet and its very small thickness, relative to that of the stagnant air layer, results in a negligible mass transfer resistance relative to that in the stagnant air layer.

A nil concentration of contaminant is maintained at the surface collector by using a substantial excess of a high efficiency collection medium. In this case, the mass transfer relationship for a purely diffusive resistance is:

$$N_{Diffusive} = \frac{DA}{\lambda} C_\infty \qquad (1)$$

N = contaminant mass flow, moles/sec.
D = contaminant diffusivity in air, cm$^2$/sec
A = diffusion path cross-sectional area, cm$^2$
$\lambda$ = diffusion barrier thickness, cm
C$_\infty$ = ambient contaminant concentration, moles/cc.

If all mass transfer for contaminant were exterior to the sampler, the mass flow would be $$N_{convective} = k A C_\infty \qquad (2)$$

where
k = the convective mass transfer coefficient

A typical minimum ambient air velocity in an enclosed room would be 10 ft/min (relative to a stationary object).

Treating mass transfer as flow over a flat plate, the Reynolds number (Re) for a 2 inch × 2 inch sampler would be:

$$Re = \frac{VL}{\nu} = \frac{\left(\frac{10}{60}\right) \frac{ft}{sec} \left(\frac{2}{12}\right) ft}{0.145 \times 10^{-3} \frac{ft^2}{sec}} = 191 \qquad (3)$$

where:
V = linear velocity over porous sheet
L = length of porous sheet in direction of flow
$\nu$ = kinematic viscosity of air (value is at 0° C)

The mass transfer coefficient can be estimated from the correlation for low Reynolds number drag (10<λRe<3000) given in Knudsen and Katz ("Fluid Dynamics and Heat Transfer," McGraw-Hill, p. 267, (1958). Using the Chilton-Colburn analogy, which is exact in this case, the mass transfer coefficient is given by:

$$Sh = \frac{kL}{D} = 1.45 \, (Re_L)^{0.4} \, (Sc)^{1/3}$$

where,
Sh = the Sherwood number,
Sc = the Schmidt number
or, $$k = 1.45 \left(\frac{D}{L}\right) (Re_L)^{0.4} (Sc)^{1/3}$$

It is interesting to note that k is only mildly dependent on the ambient air velocity ($k \propto Re^{0.4} \propto V^{0.4}$).

Values of k for different contaminants are given below

|  | SO$_2$ | NO$_2$ | O$_3$ |
|---|---|---|---|
| D(273° C, 1 atm), cm$^2$/sec | 0.122 | 0.144 | 0.141 |
| Sc = $\nu$/D | 1.23 | 1.04 | 1.06 |
| k, cm/sec | 0.29 | 0.35 | 0.34 |

As a design basis, it may be arbitrarily specified that the diffusive resistance is ten times the convective resistance. This will minimize (± 10%) any effect of ambient convection on the response of the dosimeter; that is, $$\frac{k}{D/\lambda} = 10$$

or $$\lambda = 10 \frac{D}{k}$$

For this condition, the diffusive path lengths required for the three contaminants are:

|  | SO$_2$ | NO$_2$ | O$_3$ |
|---|---|---|---|
| $\lambda$, cm | 4.1 | 4.1 | 4.1 |

This value is substantially larger than the 1 cm capillary length found to be minimum for a capillary diffusion dosimeter, and thus the diffusion path of my dosimeter could be as small as 1 cm, without introducing significant error due to air motion.

Nevertheless, a length of 4 cm is easily obtained mechanically through lengthening of the air flow path within the dosimeter. The dosimeter could then be a cube with approximate dimensions of 2 inches × 2 inches × 2 inches.

Given the dominant resistance to mass transfer in the diffusive layer, the only transport parameter sensitive to ambient temperature or pressure is the contaminant diffusivity, D. The molecular diffusivity depends on these parameters as shown in equation (4) (see Satterfied and Sherwood, "The Role of Diffusion in Catalysis", p. 5, 1963).

$$D \propto \frac{T^{3/2}}{P} \qquad (4)$$

The increase in diffusivity with an increase in temperature from 5° C to 35° C would be:

$$\left\{\left(\frac{273 + 35}{273 + 5}\right)^{3/2} - 1\right\} \times 100 = 16\%$$

Changes in barometric pressure from 28 to 32 inches Hg would lead to a decrease of 14% in the diffusivity.

Note that the amount collected is virtually independent of temperature, and completely independent of pressure. This is because $N \propto DC_\infty$. Considering temperature, $D \propto T^{3/2}$; $C_\infty \propto T^{-1}$; hence $N \propto T^{1/2}$. Considering pressure, $D \propto P^{-1}$; $C_\infty \propto P$; hence $N \propto P^0$. Thus when contaminant concentration is expressed in ppm (volume), instead of ppm (weight), $N \propto T^{1/2}P^0$.

Thus, changes in ambient conditions over the ranges anticipated will not create a significant inaccuracy in this sampling method. In addition, changes in relative humidity are completely unimportant in affecting the diffusive mass transport.

In response time considerations, the dead time of the passive device is of potential concern. A simple way of examining the dead time is to ratio the amount of contaminant held up in the stagnant diffusion zone to the amount collected per unit time. As a simplified case, assume:

$$C_{stagnant\ layer} = \frac{C_x}{2}$$

(Note C at surface collector is zero, and C at the porous layer is $C_\infty$). Then, with the stagnant Volume ($V_{stagnant}$) equal to $\lambda A$, $$\frac{\text{amount in stagnant layer}}{\text{amount collected per unit time}} = \frac{V_{stagnant} C_{stagnant}}{\frac{DA}{\lambda} C_x}$$

$$= \frac{A\lambda C_x/2}{\frac{DA}{\lambda} C_x} = \frac{\lambda^2}{2D}$$

The following times, then, are "time constants" of the system, i.e., the average residence time of contaminant in the diffusion zone ($\lambda = 4$ cm).

|  | SO$_2$ | NO$_2$ | O$_3$ |
|---|---|---|---|
| time, seconds | 66 | 56 | 57 |

Hence, response time is very short compared to the 24 hr. sampling period specified. In fact, the basic design configuration could be used for much shorter sampling times without introducing any significant error; e.g., 12, 8, 4, or even 1 hour (error only 1.7%).

By creating a diffusive resistance to mass transfer, the rate of contaminant flow to the collector is reduced. The total amount collected over a period of time, $\theta$, is $$N\theta = \frac{DAC_x\theta}{\lambda} \quad (5)$$

Assuming a 24-hr. sampling period and a minimum ambient concentration of 0.015 ppm, the minimum amount collected for a sampler can be calculated. If a dosimeter area of 25 cm² (2 inches × 2 inches) is chosen and a diffusive length of 4 cm, then from equation (5) the minimum amount collected within 24 hours at 0° C is:

| SO$_2$ | NO$_2$ | O$_3$ |
|---|---|---|
| 2.8 µg | 2.4 µg | 2.4 µg |

Therefore, any analytical procedure used subsequently to assay for the recovered contaminant should be sensitive at the 2 ug level. Furthermore, if a diffusion length of 1 cm is employed, the sensitivity need be only 10 ug.

For example, in the determination of ozone in air employing my dosimeter, one of two solutions may be employed for dipcoating a filter paper as the collecting medium:

1,2-di(4-pyridyl)ethylene in glacial acetic acid; or
4,4-dimethoxystilbene in sym tetrachloroethane.

After coating, the sheets are dried and packaged for subsequent insertion into the dosimeter.

The method of Bravo and Lodge (see Analytical Chemistry, 36, p. 671, 1964) via anisaldehyde is then employed to analyze the concentration of ozone.

The procedure of Bravo and Lodge is based on the cleavage of 4,4'-dimethoxystilbene CH$_3$O C$_6$H$_4$ CH=CH C$_6$H$_4$ O CH$_3$ by ozone to form anisaldehyde, which, together with fluoranthene and trifluoroacetic acid, produces an intense blue.

Calibration curves are plotted by weighing anisaldehyde and measuring the color intensity in accordance with the above prescription. The authors indicated a 98% yield, assuming that 1 mole of ozone yields only 1 mole of aldehyde in the reaction with stilbene. The molar extinction coefficient is 35,000, the detection limit in 8 liters air is 10 ppb (0.2 ug). The following substances do not interfere, provided they occur in amounts below 1 ppm: NO$_2$, peroxyacetyl nitrate, methylhydroperoxide. SO$_2$ does not interfere even at slightly higher concentrations.

The method of Hauser and Bradley (see Analytical Chemistry, 38, p. 1529, 1966) via pyridine-4-aldehyde may also be used where it is desired to avoid the use of corrosive trifluoroacetic acid in a spectrophotometer. Hauser and Bradley employed 1,2-di(4-pyridyl)ethylene in glacial acetic acid. The pyridine-4-aldehyde formed is determined with the aldehyde reagent 3-methyl-2-benzothiazolinone hydrazone. In this case, however, it is more appropriate to work without the addition of FeCl$_3$. Instead of the blue color, an intense yellow reaction product is formed and the extinction measured at 442 mu.

The coated sheets with the ozone collected are extracted after exposure, with the solvent originally used for coating. This is followed for either method with the procedures given above. The sensitivity of these procedures should be below 1 ug, which will be adequate based on the amount of O$_3$ which will diffuse into the collection medium over a 24-hr. period.

For the collection and determination of sulfur dioxide, an impregnated filter paper may be used with a technique already developed for ambient SO$_2$ analyses.

Huygen (see Anal. Chim. acta, 28, p. 349, 1963) and Pate, Lodge and Neary (see Anal. Chim. acta, 28, p. 341, 1963) use alkali-treated filter papers, which are washed out after sampling. In the washings, SO$_2$ is determined according to the method of West and Gaeke (see Analytical Chemistry, 28, p. 1816, 1956).

Filter papers (Whatman No. 1) are immersed in the absorption solution described below, and the excess solution is removed by dabbing. In this way, an uptake of about 10 mg solution per cm² filter area is achieved. The filter papers are dried at 110°C. The absorption solution used is an aqueous solution containing 20% KOH and 10% triethanolamine or glycerol.

The impregnated filter is mounted as the collector sheet on the back face of the dosimeter behind the diffusive barrier element. After the filter collector has been exposed by the test subject and returned to the laboratory, it will be extracted and $SO_2$ will be determined according to West and Gaeke.

On the basis of the Schiff reaction between pararosaniline, formaldehyde and sulfur dioxide, which has been used in analytical chemistry for a long time for the detection of both $SO_2$ and formaldehyde, several methods for the quantitative colorimetric determination of $SO_2$-traces were developed in air analysis. The variant of West and Gaeke is the most widespread of these methods. The authors employed the data of Feigl on the stability of the disulfitomercurate ion $(Hg[SO_3]_2)^{2-}$ and used A sodium tetrachloromercurate solution (from $2 NaCl + HgCl_2$), in which $SO_2$ remains stable for at least 24 hrs. as the absorption solution for the $SO_2$ in the air sample.

0.5 ug of $SO_2$ corresponds to an extinction of 0.015. Nitrogen dioxide interferes when present in concentrations exceeding 2 ppm.

The impregnated filter is extracted with an $Na_2HgCl_4$ solution. To this extract, the other reagents are added, and absorbance measured.

The sensitivity of this procedure is below 1 ug, which is adequate based on the amount of $SO_2$ which will diffuse into the collection medium over a 24-Hr. period.

For the collection and determination of nitrogen dioxide, an impregnated solid (filter paper) is used with a technique already developed for $NO_2$, as well as $SO_2$.

Levaggi, Siu and Feldstein (JAPCA, 23, p. 30, 1973) have developed a technique for a solid absorber (impregnated molecular sieve) for determining $NO_2$. After sampling ambient air, the solid absorber is extracted and the extract analyzed by the Saltzman method.

The principle for both $SO_2$ and $NO_2$ absorption processes is the same; i.e., absorption of an acid gas in an alkaline medium. The alkaline medium of Levaggi et al is used to impregnate filter paper according to the method of Huygen.

The reagent (see Saltzman, Analytical Chemistry, 26, p. 1959, 1954 and 32, p. 135, 1960) contains instead of $\alpha$-naphthylamine as the coupling component in the Griess reagent N-(1-naphthyl)-ethylenediamine. The Saltzman reagent was previously used for the determination of the sulfonamide medicament sulfanilamide and is now frequently used for the determination of nitrite, for example, in water.

In order to obtain air samples with $NO_2$-levels below 1 ppm, Saltzman used a small fritted scrubber containing 10 ml absorption reagent. The air sample is introduced at a rate not exceeding 0.4 liter/min; 20–30 ml fine foam formed over the solution. For $NO_2$-levels exceeding 1 ppm, the sample is drawn into an evacuated vessel of known volume and containing 10 ml absorption solution. The sample sampling is carried out in vacuum.

The solution is allowed to stand for at least 15 min, and the extinction is measured with the spectrophotometer against fresh reagent at 550 mu. The color is retained in a heremetic flask for 1 day with only 3–4% fading.

The calibration curve is plotted for dilute $NaNO_2$ solution (e.g., 10 ug $NaNO_2$/ml). Saltzman, however, did not assume that 1 mole $NaNO_2$ is equivalent to 2 moles $NO_2$ in accordance with the equation $2NO_2 + H_2O = HNO_2 + HNO_3$, but found in his procedure that 0.72 mole (instead of 0.5 mole) $NaNO_2$ gives the same color as 1 ml $NO_2$ in test air mixtures.

A 10-fold $SO_2$ concentration does not appreciably interfere. When more $SO_2$ is expected, 1% acetone is added to the absorption solution and the determination is carried out no later than 4 or 5 hrs. afterward.

Ozone, interfering in concentrations above 0.2 ppm, can be removed without any $NO_2$ losses by passing the air through a glass wool plug impregnated with $MnO_2$. The plug is prepared by impregnating glass wool with an $MN(NO_3)_2.6H_2O$ solution, and then heating in a 200° C air streamm until all the nitrogen oxides have been expelled. This approach, if required, could be implemented by impregnating the porous sheet covering the sampler with $MnO_2$, and replacing the sheet periodically.

Absorption reagent used is 5 g sulfanilic acid dissolved in 850 ml water, 50 ml glacial acetic acid and 50 ml 0.1% N(1-naphthyl)ethylenediamine dihydrochloride solution added. The volume is then made up to 1000 ml.

The impregnated filter collector is extracted with the absorption reagent, and the Saltzman procedure followed to determine the $NO_2$ concentration.

The sensitivity of this procedure should be below 1 ug, which is adequate based on the amount of $NO_2$ which will diffuse into the collection medium over a 24-hr. period.

Figure 1:
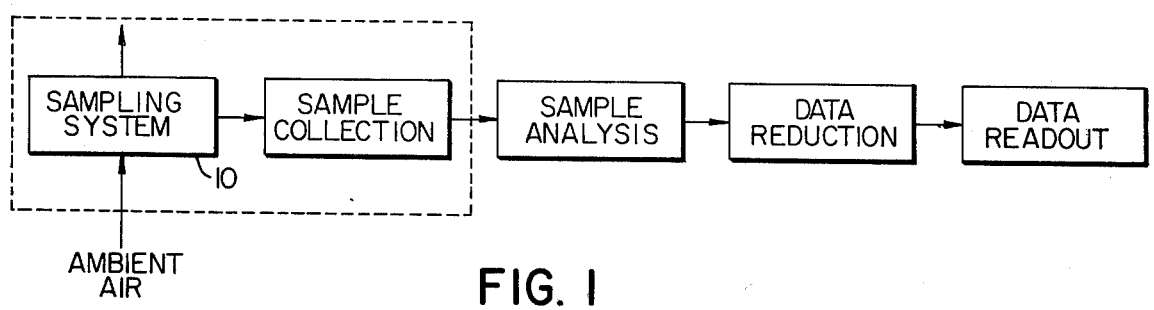
FIG. 1 is a schematic illustrative block diagram of a system of employing my dosimeter.

The method of use of the dosimeter is as set forth in block diagram in FIG. 1 and is as follows: The dosimeter is delivered to the user with a supply of surface collectors in sealed impermeable packets. The subject will open one packet, and remove and insert one collector in the sampler. The subject will then affix the sampler to his or her lapel, belt, etc. After wearing the sampler for a specified period; e.g., a 24-hr. period, the subject will open the dosimeter and remove the surface collector. The subject will seal the surface collector in an impermeable mailing container provided, and mail to the designated analytical laboratory for analysis. The subject will remove a new collector from an unopened packet, place in the sampler, close the sampler, and repeat the exposure test procedure. Thus, the test subject will be responsible only for extremely simple operations, which are not expected to be sensitive to variations in test subject behavior.

This approach is designed to provide a 24-hr. composite sample. If, however, it is desirable to obtain time resolution during this period, a modification of the dosimeter and method can be used.

My dosimeter has been described in regards to the preferred structure, tests and embodiments; however, it is recognized and is a part of my invention that other methods for providing collection means may be used, depending on the contaminates to be determined, such as solid; e.g., submicron, particles. In addition, means may be used to expose selectively various parts of the collecting medium to the gaseous environment so as to obtain a cumulative determination of contaminates, such as by exposing only a portion of the collecting medium to the gaseous stream for a defined period of time.

What is claimed is:

1. A passive gaseous contaminate dosimeter to determine the amount of gaseous contaminates in a gas stream, which dosimeter comprises in combination:
   a. a closed container;
   b. a gaseous contaminate collecting medium of a solid or liquid sorbent within the interior of the container, which medium sorbs or reacts with the gaseous contaminate, the amount of which is to be determined;

c. an inert porous sheet barrier element forming a portion of at least one side of the container, which barrier element permits the diffusion freely of the gas stream containing the gaseous contaminate from the ambient atmosphere into the interior of the container;

d. a dead air space between and separating the barrier element and the collecting medium;

e. the barrier element characterized by having a low diffusional resistance to the gas stream with the gaseous contaminate relative to that of the dead air space to permit the collection on the collecting medium of gaseous contaminates which diffuse into the interior of the container in proportion to the average ambient concentration about the dosimeter, and substantially independent of the ambient convection patterns of the gas stream exterior to and about the dosimeter; and f. a plurality of passageways extending within the dead air space to provide mechanical support to the sheet barrier element.

2. The dosimeter of claim 1 wherein the barrier element has a porosity of from about 50 to 95%.

3. The dosimeter of claim 1 wherein the barrier element has a thickness ranging from about 0.001 cm to 0.8 cm.

4. The dosimeter of claim 1 wherein the barrier element comprises a porous sheet material composed of a polymer, metal or glass.

5. The dosimeter of claim 1 wherein the passageways are composed of a plurality of elongated generally uniformly spaced honeycomb passageways which extend from the interior face of the barrier element and toward the opposing gaseous contaminate collecting medium, and which divides the interior of the dead air space into a plurality of separate space volumes by permitting the passage of the gas stream containing the gaseous contaminate from the internal face of the barrier element through the passageways to the collecting medium.

6. The dosimeter of claim 5 wherein the passageways comprises a rigid polymeric structure of generally parallel and spaced apart walls, the walls substantially perpendicular to the internal face of the barrier element, and the honeycomb element extending from the internal face of the barrier face to the base of the collecting medium in the dead air space.

7. The dosimeter of claim 1 wherein the collecting medium comprises a removable sheet material impregnated with a solid or liquid material to sorb or react with the gaseous contaminates of the gas stream, the sheet element directly opposite the barrier element and separated by the dead air space.

8. The dosimeter of claim 1 wherein the collecting means comprises a paper sheet impregnated with an agent which sorbs or reacts with sulfur dioxide, nitrogen dioxide, vinyl chloride, carbon monoxide, hydrogen sulfide or ozone.

9. The dosimeter of claim 1 wherein the diffusional resistance in the dead air space of the dosimeter is over five times the diffusional resistance of the convective mass transfer exterior to the dosimeter.

10. A passive gaseous contaminate dosimeter to determine the amount of gaseous contaminate in a gas stream, which dosimeter comprises in combination:

a. a small, light-weight, closed container adapted to be employed on or about the breathing zone of a user;

b. a gaseous contaminate collecting medium composed of a sheet material impregnated with a solid or liquid sorbent within the container, which collecting medium sheet sorbs or reacts with the gaseous contaminate of the gas stream whose amount is to be determined;

c. an inert porous thin sheet barrier element forming a portion of at least one side of the container, and which permits diffusion freely of the gas containing the gaseous contaminate into the interior of the container, the barrier element having a thickness of from about 0.001 to 8 cm, and a porosity of from about 50 to 95%;

d. a dead air space between and separating the barrier element and the sheet collecting medium;

a plurality of passageways extending within the dead air space to provide mechanical support to the sheet barrier element; and f. the barrier element characterized by having a low diffusional resistance to gaseous contaminates in the gas stream relative to that of the baffle dead air space to permit the collection on the collecting medium of gaseous contaminates from the gas stream in proportion to the average ambient concentration of the gas stream and substantially independent of the ambient convection gas patterns of the gas stream about the exterior of the dosimeter.

11. The dosimeter of claim 10 wherein the collecting medium comprises a sheet material coated or impregnated with a solid or liquid sorbent in an amount in excess of the amount to react with the gaseous contaminate from the gas stream in a designated time period of use of the dosimeter.

12. The dosimeter of claim 10 wherein the passageways comprises a plurality of elongated straight-spaced passageways which extend from the interior face of the barrier element to the collecting medium to provide support for the thin barrier element and to retain the collecting medium adjacent the interior wall of the container.

13. In a method of determining the amount of gaseous contaminates in a gas stream during a designated time period by a dosimeter, which dosimeter comprises in combination: a closed container; a gaseous contaminate collecting medium of a solid or liquid sorbent within the interior of the container, which medium sorbs or reacts with the gaseous contaminate, the amount of which is to be determined; an inert porous sheet barrier element forming a portion of at least one side of the container, which barrier element permits the diffusion freely of the gas stream containing the gaseous contaminate into the interior of the container a dead air space between and separating the barrier element and the collecting medium; and the barrier element characterized by having a low diffusional resistance to the gaseous contaminate relative to that of the dead air space, the method which comprises:

a. diffusing a gas stream containing gaseous contaminate ambient and external of the dosimeter through the porous barrier element into the dead air space of the dosimeter;

b. providing a stagnant gaseous diffusion barrier layer inside the chamber and adjacent the interior surface of the barrier element, which stagnant air layer is substantially unaffected by ambient and gaseous patterns exterior to the opposing side of the barrier element, the resistance to mass transfer and the stagnant gaseous layer within the container substantially exceeding the resistance associated with the convective mass transfer to the porous barrier element;

c. providing a baffle element having a plurality of passageways as a mechanical support for the sheet barrier element extending between the barrier element and the collecting medium;

d. sorbing the gaseous contaminates from the diffused gas stream within the dead air space onto the gaseous collecting medium; and, thereafter, e. determining the concentration of the gaseous contaminate so collected and so sorbed.

14. The method of claim 13 wherein gaseous contaminates comprise the oxides of sulfur, the oxides of nitrogen, ozone, carbon monoxide, hydrogen sulfide, vinyl chloride, other organic vapors or gaseous contaminates, or combinations thereof.

15. The method of claim 13 wherein the gaseous contaminate collecting medium comprises a removable sheet material containing the solid or liquid sorbent, and which includes the step of removing the sheet collecting medium from the dosimeter after a designated time period, and determining the concentration of the gaseous contaminate collected, which includes providing a diffusional resistance within the dosimeter dead air space which substantially exceeds by over five times the diffusional resistance of the convective mass transfer exterior to the dosimeter.

16. The method of claim 13 wherein the gaseous contaminate collecting medium comprises a liquid or solid sorbent material which is in excess of the expected gaseous contaminate to be sorbed or reacted during the designated time period.

17. The method of claim 13 which includes providing a plurality of elongated generally uniformly spaced honeycomb passageways which extend from the interior face of the barrier element and toward the opposing gaseous contaminate collecting medium, and which divides the interior of the dead air space into a plurality of separate space volumes by permitting the passage of the gas stream containing the gaseous contaminate from the internal face of the barrier element through the passageways to the collecting medium.

* * * * *

UNITED STATES PATENT OFFICE
CERTIFICATE OF CORRECTION

PATENT NO. : 3,985,017
DATED : October 12, 1976
INVENTOR(S) : Robert L. Goldsmith It is certified that error appears in the above-identified patent and that said Letters Patent are hereby corrected as shown below:

Column 12, claim 10, part c., line 15, "8 cm" should read --0.8 cm--.

Signed and Sealed this

Twenty-fifth Day of January 1977

[SEAL]

Attest:

RUTH C. MASON
Attesting Officer

C. MARSHALL DANN
Commissioner of Patents and Trademarks